United States Patent
Robinson et al.

(10) Patent No.: US 9,107,973 B1
(45) Date of Patent: Aug. 18, 2015

(54) ENCLOSURE TO DISINFECT LAB COATS AND OTHER TEXTILES AND OBJECTS OF SIMILAR SIZE TO LAB COATS

(71) Applicants: Jeffrey D. Robinson, Charlotte, NC (US); Joseph H. Pride, Chapel Hill, NC (US); Mark G. Deveau, Canton, GA (US)

(72) Inventors: Jeffrey D. Robinson, Charlotte, NC (US); Joseph H. Pride, Chapel Hill, NC (US); Mark G. Deveau, Canton, GA (US)

(73) Assignee: dReiniger, LLC, Charlotte, NC (US)

( * ) Notice: Subject to any disclaimer, the term of this patent is extended or adjusted under 35 U.S.C. 154(b) by 0 days.

(21) Appl. No.: 14/678,041

(22) Filed: Apr. 3, 2015

Related U.S. Application Data

(60) Provisional application No. 61/977,197, filed on Apr. 9, 2014.

(51) Int. Cl.
*A61L 2/22* (2006.01)
*A61L 2/24* (2006.01)
*A61L 2/10* (2006.01)

(52) U.S. Cl.
CPC ... *A61L 2/22* (2013.01); *A61L 2/10* (2013.01); *A61L 2/24* (2013.01)

(58) Field of Classification Search
CPC .......................................... A61L 9/14
USPC ................ 250/455.11; 422/28, 292, 294, 295
See application file for complete search history.

(56) References Cited

U.S. PATENT DOCUMENTS

| | | | |
|---|---|---|---|
| 6,068,815 A * | 5/2000 | Oberleitner et al. ............ 422/28 |
| 6,706,243 B1 * | 3/2004 | Sias et al. ........................ 422/28 |
| 7,138,087 B1 * | 11/2006 | Malkin et al. .................. 422/26 |
| 8,303,905 B2 * | 11/2012 | Brents et al. ................. 422/292 |
| 8,459,050 B2 * | 6/2013 | Hipp ............................... 62/115 |
| 8,484,867 B2 * | 7/2013 | Roselle et al. ..................... 38/14 |
| 8,671,855 B2 * | 3/2014 | Capote et al. ................ 110/250 |
| 8,847,174 B2 * | 9/2014 | Domenig et al. ........ 250/455.11 |
| 9,024,277 B2 * | 5/2015 | Domenig et al. ........ 250/455.11 |
| 2004/0003511 A1 * | 1/2004 | Silver .............................. 34/201 |
| 2013/0199581 A1 * | 8/2013 | Christopherson .......... 134/103.2 |

FOREIGN PATENT DOCUMENTS

EP      0486623 B1    1/1997

* cited by examiner

*Primary Examiner* — David A Vanore
(74) *Attorney, Agent, or Firm* — Steven Critzer

(57) ABSTRACT

An apparatus for sterilizing and disinfecting medical garments such as lab coats, shoes, and related medical equipment using an electrostatically charged nozzle to deliver high velocity air or steam carrying atomized chemical or antimicrobial treatments. The top chamber is designed to hold a removable supporting member or hanger which is used to hold the garments and equipment being sterilized and disinfected. The top chamber is both electrically and thermally insulated. The bottom chamber is designed to house the various reservoirs, pumps, and generators used to perform the treatment operations. The bottom chamber is a drawer so the reservoirs can easily be refilled and alternative pumps or generators can be installed.

7 Claims, 6 Drawing Sheets

ENCLOSURE TO DISINFECT LAB COATS AND OTHER TEXTILES AND OBJECTS OF SIMILAR SIZE TO LAB COATS

STATEMENT REGARDING FEDERALLY SPONSORED RESEARCH OR DEVELOPMENT

Not Applicable

BACKGROUND

Due to frequent use of antibiotics, hospitals and healthcare facilities are at high risk of breeding antibiotic-resistant bacteria (superbugs). When a person acquires a Hospital-Acquired Infection (HAI) involving a superbug and their body is incapable of resisting infection on its own, few effective treatments are available. According to the Center for Disease Control, patients in the U.S. contract nearly 2 million HAIs each year that contribute to around 99,000 deaths. The cost to the Healthcare system is estimated to be in the tens of billions of dollars annually. Not every HAI can be effectively treated once contracted; the best cure is prevention before the infection occurs, through effective sanitation of every vector that can transmit infection from one patient to another, permit infection to travel from place to place, or create a conducive environment for live bacteria to persist over time.

One transmission vector generally regarded as high-risk is through physical contact with healthcare professionals. Patients less frequently have physical contact with each other, but healthcare professionals move continually from patient to patient. While healthcare professionals are encouraged to adopt habits of personal hygiene and frequent hand washing, the fabrics of their clothes, being porous and less frequently washed, may be more hospitable environments for germs to travel from patient to patient. Superbugs such as MRSA have been demonstrated to live on articles of clothing for weeks.

In addition to the personal risk to patients and doctors, HAIs also create financial risk for hospitals. Hospitals face increasing levels of liability for the care of patients.

So, for both humanitarian and financial reasons, hospitals have a clear need to reduce the number of HAIs.

Many articles of clothing in hospitals, including scrubs, are either disposable or interchangeable and are cleaned in bulk. But while similar services exist, various factors of inconvenience result in less-frequent cleaning for hospital lab coats, doctor's shoes, and a few other personal medical items such as stethoscopes that remain with one doctor day after day. For this reason, lab coats, shoes, and a few other personal medical items of similar and smaller size may present a heightened risk of causing infection. Setting the risk aside, these items also cause the perception of risk, which may lead to increased anxiety by patients and healthcare professionals.

This invention is designed to deliver additional convenience in disinfecting lab coats, helping healthcare professionals to disinfect their garments, shoes, and personal medical items far more frequently than they have done previously and helping patients and healthcare professionals to feel safer about HAIs.

SUMMARY

The present invention is directed to an apparatus that satisfies the need for a convenient way to quickly and easily disinfect medical garments such as lab coats, shoes, and other personal medical items such as stethoscopes. The apparatus comprises a top chamber which is both electrically and thermally insulated and contains a rod at the top running axially from front to back as well as an electrostatically charged delivery nozzle at the bottom, a bottom chamber which houses various reservoirs, generators, and compressors in a service drawer as well as access holes to allow electrical or plumbing connections or nesting of multiple units together, a control mechanism, and a supporting member which can glide on and off of the rod in the first chamber. The apparatus can include ultraviolet-C lights inside the top chamber to disinfect the contents of the top chamber. The apparatus can include a means for detecting and authenticating the garments or equipment placed inside the top chamber, such as a radio-frequency identification (RFID) scanner. The control mechanism can either be manual or electronic. The electronic control mechanism can be programmable and capable of relaying data information to other computers over information networks such as the Internet.

BRIEF DESCRIPTION OF THE DRAWINGS

These and other features, aspects, and advantages of the present invention will become better understood with regard to the following description, appended claims, and accompanying drawings where:

DESCRIPTION

In the Summary above and in the Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and the invention generally.

The term "comprises" and grammatical equivalents thereof are used herein to mean that other components are optionally present. For example, an article "comprising" components A, B, and C can consist of components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm.

This apparatus uses multiple attacks to deactivate or destroy bacteria and treat objects within the apparatus in order to provide residual protection against bacteria. This apparatus may also be applicable to other uses including but not limited to finishing and coating processes in manufacturing, curing light-sensitive materials, or steam-treating solids, textiles, or foods to produce material, chemical, or aesthetically desirable results such as softening wood for bending.

Figure 1:
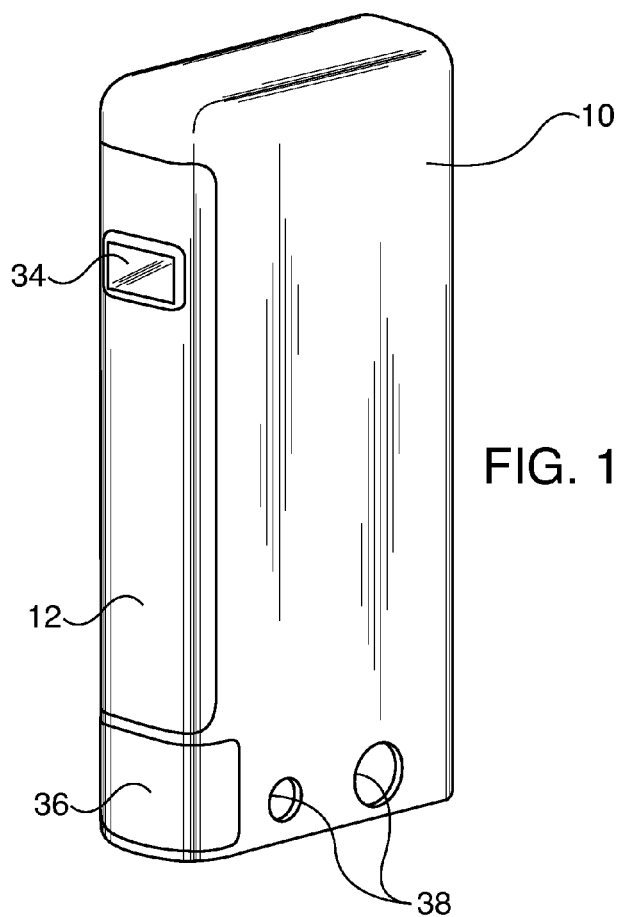
FIG. 1 shows a perspective view of an apparatus embodying features of the present invention.
Figure 2:
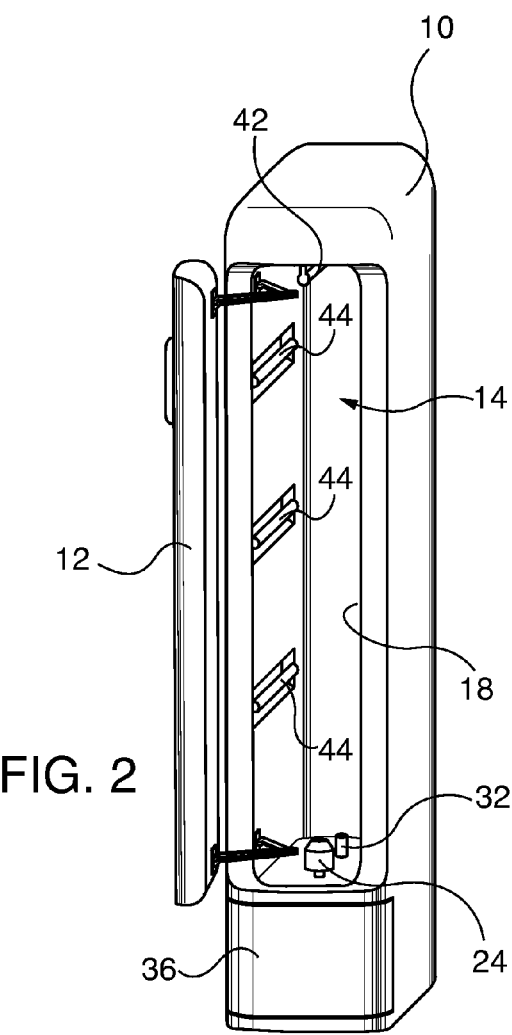
FIG. 2 shows a front view of the apparatus of FIG. 1 with the cabinet door open.
Figure 3:
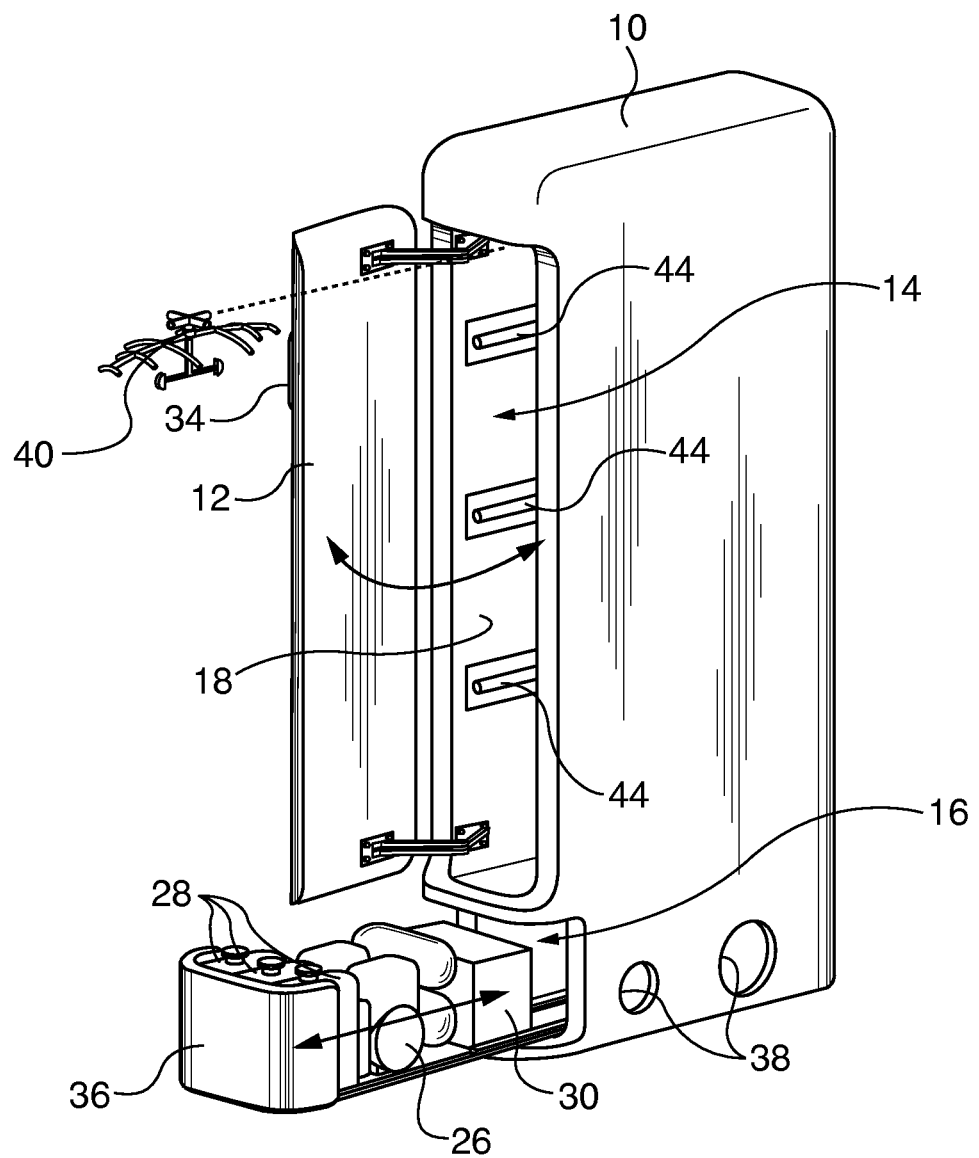
FIG. 3 shows a perspective view of the apparatus of FIG. 1 with the cabinet door open, the service drawer open, and the supporting member removed.
Figure 4:
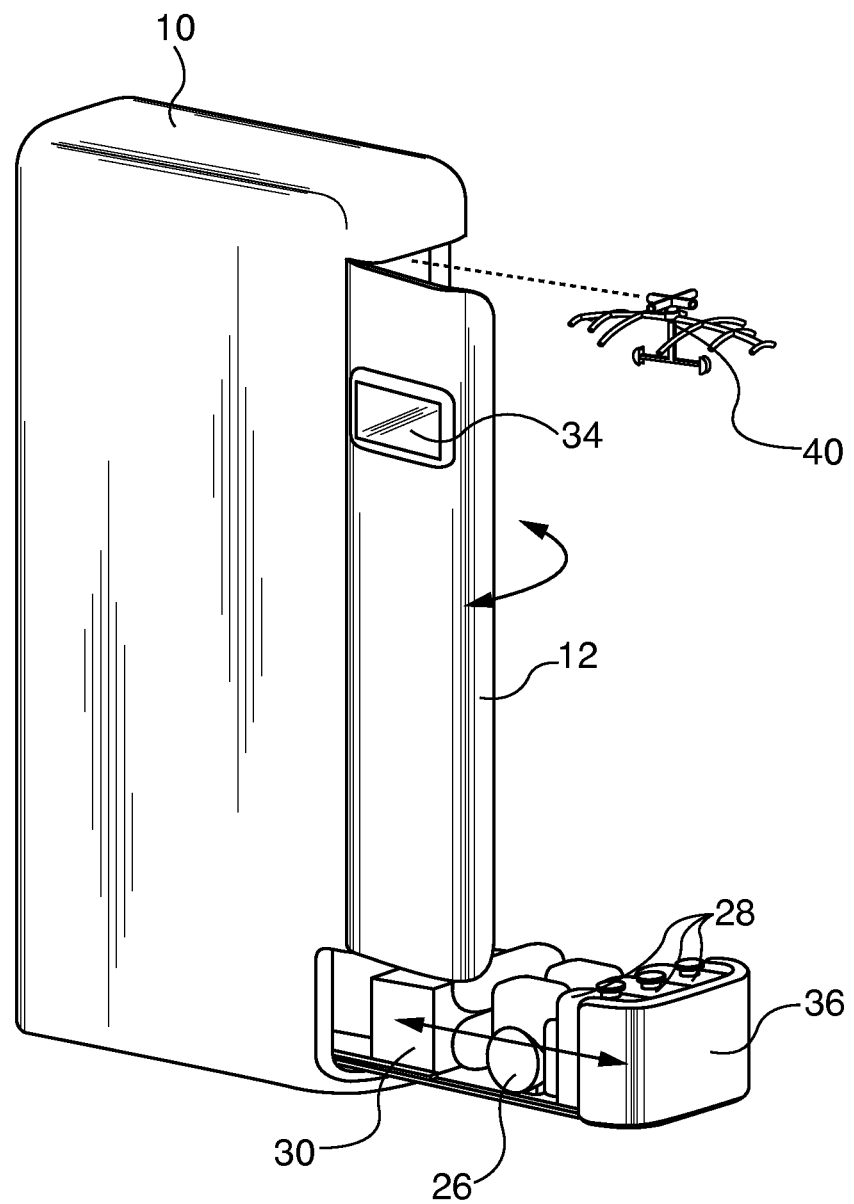
FIG. 4 shows a perspective view of the apparatus of FIG. 1 from the other side with the cabinet door open, the service drawer open, and the supporting member removed.
Figure 5:
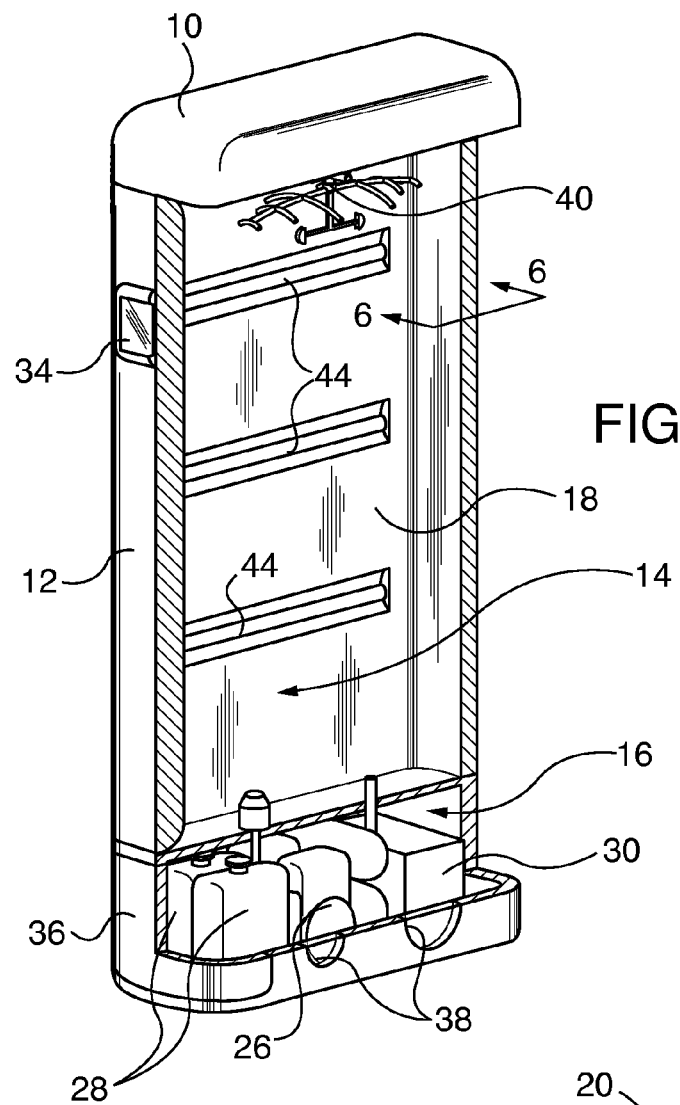
FIG. 5 shows a "cut-away" view of the apparatus of FIG. 1.
Figure 6:
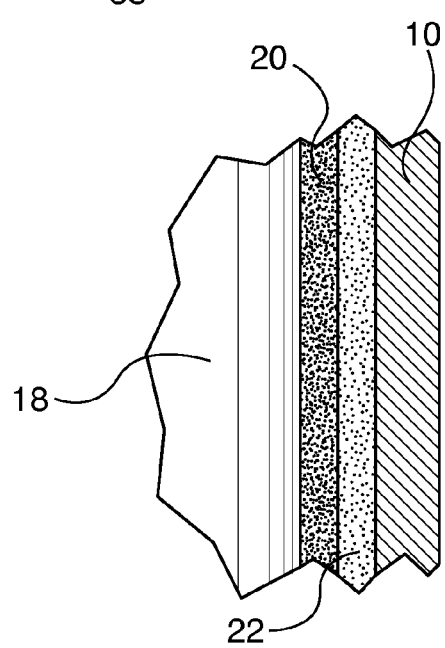
FIG. 6 shows a close-up "cut-away" view of the top chamber wall as shown and labeled in FIG. 5.
Figure 7:
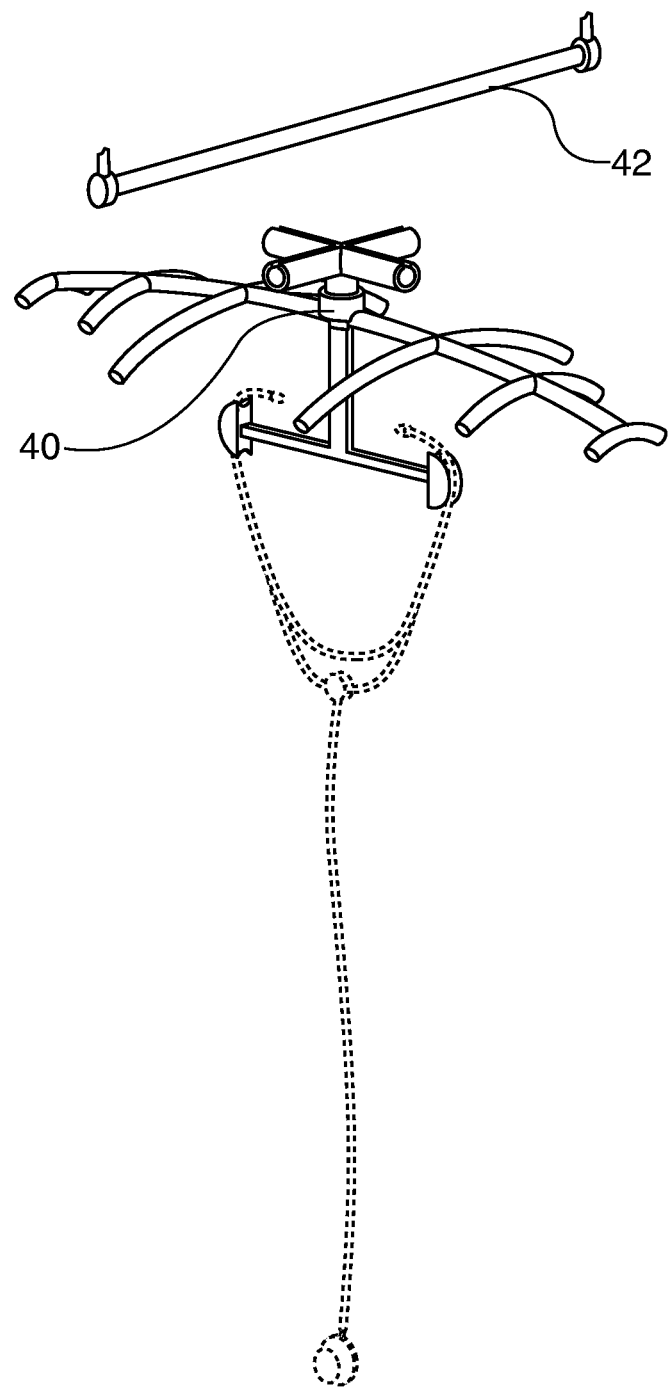
FIG. 7 shows a perspective view of the supporting member which hangs inside the apparatus of FIG. 1 and the rod from which the supporting member hangs.
Figure 8:
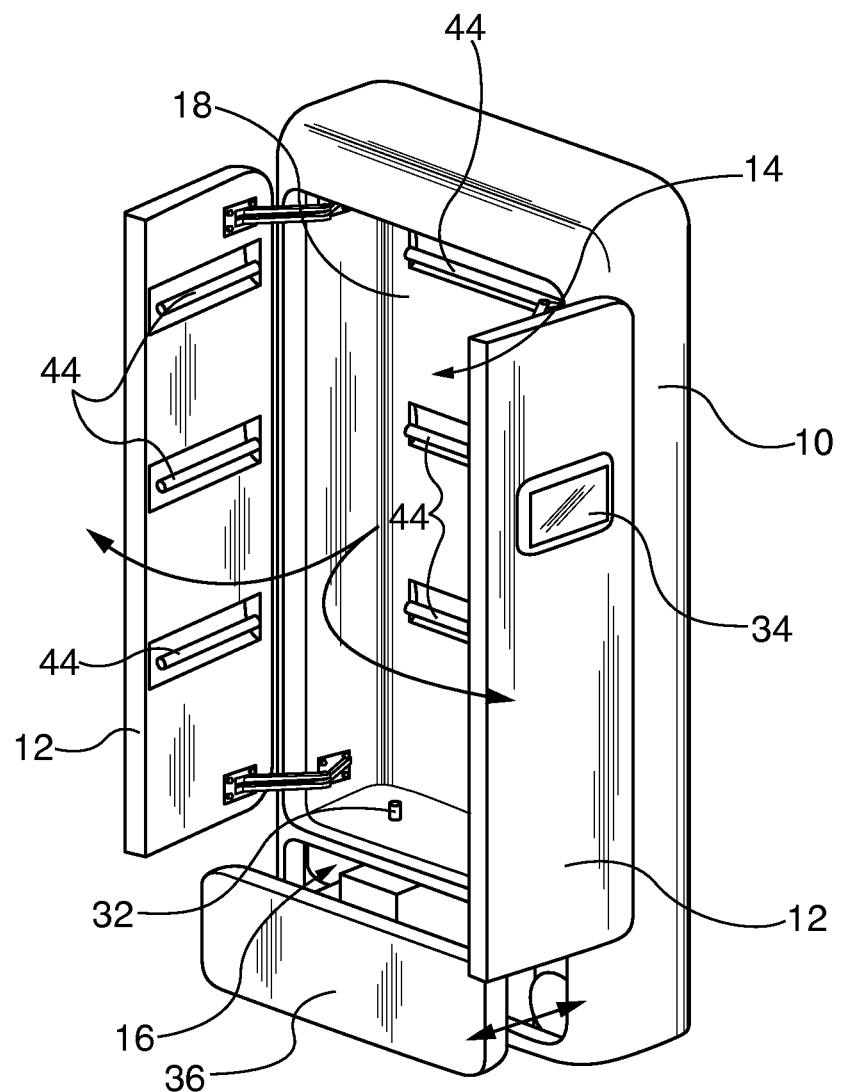
FIG. 8 shows a perspective view of an alternative version of an apparatus embodying features of the present invention.

As shown in FIG. 1, the apparatus entitled "an enclosure to disinfect lab coats and other textiles and objects of similar size to lab coats" consists of a cabinet 10, a cabinet door 12, a control mechanism 34, a service drawer 36, and access holes 38. As shown in FIG. 2, the apparatus also consists of a top chamber 14, an inner lining 18, a delivery nozzle 24, a steam pressure relief exhaust valve 32, and a rod 42. FIG. 2 also shows the optional feature of UV lights 44. As shown in FIG. 3, the apparatus also consists of a bottom chamber 16, a compressor 26, reservoirs 28, a steam generator 30, and a supporting member 40 such as a hanger. As shown in FIG. 6, the walls of the top chamber 14 of the cabinet 10 consist of an inner lining 18, an outer lining 20, and an interstitial zone 22.

In the preferred embodiment, disinfection and treatment can be accomplished with an apparatus that uses steam, ultraviolet light in the spectrum of 200 to 320 nanometers of wavelength (UVC light), and an atomized liquid chemical treatment. The top chamber 14 may be sized with minimum internal dimensions that accommodate most sizes of lab coats and shoes.

In a variation on the above embodiment, disinfection and treatment can be accomplished via only a subset of the named disinfection and treatment techniques.

In a variation on the above embodiment, the atomized liquid chemical treatment may include the availability of multiple liquid chemicals, either in combination or with the option to select between them to use only a single chemical as a subset of the multiple chemicals available in the cabinet 10.

In a variation on the above embodiment, in addition an electrolyzing device may be used to generate electrolyzed water, also known as oxidizing water, which can also be also be delivered via the same or a separate atomizing process as that used for other chemical treatments.

In an alternative embodiment which may include some or all the possible methods of treatment as described above, the top chamber 14 may be sized to enable multiple lab coats to be treated at once and may include lighting arrangements that ensure spaces between coats are treated with the ultraviolet light 44.

Alternatively, multiple single-coat cabinets 10 may be combined together into a single device that may operate each compartment with separate simultaneous cycles, yet use a single central infrastructure of machinery to generate the treatment.

Alternatively, multiple single-coat cabinets 10 may be combined together into a single assembly that provides autonomous machinery for each compartment, each compartment being individually equivalent to a separate single-coat apparatus.

In another embodiment, disinfection and treatment can be accomplished for smaller items with an apparatus that uses the disinfection techniques described in the previous embodiments but carries out disinfection in a smaller top chamber 14 with internal dimensions sized appropriately for shoes, stethoscopes, endoscopes, and other small items, using disinfection tools also scaled appropriately for the smaller apparatus.

The preferred liquid chemical treatment is water-based and unscented, but other liquid chemical treatments based in oil, or other solvents may be used, and additional scents, fresheners, antibiotics, antiseptic compounds, alcohols, proprietary chemicals, or other liquid ingredients could be added. Steam may be delivered either under pressure or at atmospheric pressure, under wet, saturated, or superheated conditions; medical literature indicates that saturated or slightly superheated conditions are most ideal for sterilization, but other conditions of steam may be useful for other applications.

In the preferred embodiment of steam delivery, steam is generated by passing water through an in-line steam generator 30 held at a constant temperature with an electrical power source. Steam is generated at a constant rate by the in-line generator 30; the steam volume is controlled by controlling the flow of supply water. Water is supplied either from an internal reservoir 28 or an external water connection and may be pumped through a valve, which can open or close to throttle or hold back the water. Either the valve or the pump itself may be controlled in order to control the flow of supply water to the steam generator 30, thereby controlling the volume of steam generated.

In another embodiment, steam is generated as described in the above paragraph, except using natural gas or another combustible fuel to generate the heat and controlling the quantity and ignition of the fuel to regulate temperature.

In another embodiment, steam is generated under pressure by use of an electrical heating element installed into a small pressure vessel just small enough to contain the heating element. This minimizes the amount of liquid water which must be heated at any time. As the water is converted to steam, it passes through tubing from the top of the small pressure vessel into a larger pressure vessel. The low point on the larger pressure vessel drains by gravity back into the small pressure vessel. This ensures that water is concentrated around the heating element and that the larger pressure vessel is used entirely to contain saturated steam. By using a level switch or other means of transmitting or monitoring the level of the saturated water, the water level can be controlled to ensure the heating element remains submerged at all times. As water is converted to steam and the water level slightly falls, additional water may be introduced into the steam generator 30 from an outside water source by means of a pump capable of exceeding the chamber pressure, so that the water level remains high enough to submerge the heating element but not so high as to flood the larger pressure vessel. Under these saturated conditions, both pressure and temperature can be controlled with a single measurement, which may represent either pressure or temperature. When pressure or temperature are sufficient to operate the chemical delivery mechanism and before they approach safety limits, a pressure or temperature switch or an electronic logic controller sensitive to the measurement can break the circuit to the heating element, then reconnect the heating element when pressure or temperature fall below a minimum target. The target temperature or pressure may be varied as needed for individual treatment regimens. When the steam reaches the target temperature and pressure, it may be released by a valve to activate both steam delivery and the chemical delivery mechanism. The release valve may be controllable so as to allow any fraction of the pressure and volume generated in the pressure vessel to be introduced into the steam or chemical delivery mechanism. For safety, the accumulating steam vessels must be fitted with a pressure relief exhaust valve 32 capable of releasing steam if the pressure rises beyond safe limits and a temperature cutoff switch that cuts all power if the temperature of the heating element passes safe limits. As a final precaution, the pressure vessels should be housed in a metal enclosure separate from the user-serviceable portions of the invention, such that if the pressure vessels were to rupture, any flying particles would be contained safely.

In another embodiment, steam is generated as described in the above paragraph, except using natural gas or another combustible fuel to generate the heat and controlling the quantity and ignition of the fuel to regulate temperature.

In another embodiment, steam is generated within a steam generator 30 as described in the previous two paragraphs, except that instead of the heating element and liquid water being present in a small vessel while gaseous steam is accumulated in a large pressure vessel, both the liquid water and saturated steam are present within a single pressure vessel.

In another embodiment, steam is generated by feeding water either from a pump or by gravity into a perforated heated platform similar in design and function to that commonly employed in a clothes iron. The steam is then permitted to rise through the top chamber 14.

In another embodiment, the apparatus may not generate its own steam but may receive steam from an external steam source such as steam plumbing, which may be controlled and released via controllable valves and nozzles.

In one embodiment, the inner lining 18 of the top chamber 14 is comprised of plastic. The plastic interior may include microbe-resistant materials.

In the preferred embodiment, the inner lining 18 of the top chamber 14 may be made of metal instead of plastic. The metal may be powder-coated with materials known for antibacterial effects. The metal is preferably made of aluminum, but could also be made if stainless steel, copper, or other similar metals. Aluminum is particularly favored for its reflectivity of short ultraviolet light wavelengths. The inner lining 18 may be formed into parabolic shapes focused at each ultraviolet light source 44 in order to enhance even dispersion of ultraviolet light across the items placed into the top chamber 14. In addition to the material chosen for the inner lining 18 of the top chamber 14, the inner lining 18 may have mounted mirrors in order to enhance the effectiveness of delivering ultraviolet light to all surfaces of the garments placed inside. Of particular importance, these mirrors should either be first-surface (also known as front-surface) mirrors, in which the reflective coating is applied to the front, not the back, of the mirror, thereby ensuring ultraviolet light is not absorbed by the glass, or the mirrors should be comprised of special glass formulations known to have low absorption of light in the ultraviolet-C spectrum. These mirrors may entirely line the interior of the top chamber 14 or may partially line the interior, centered on the location of each ultraviolet light source 44. These mirrors may be formed into parabolic shapes focused at each ultraviolet light source 44 in order to enhance even dispersion of ultraviolet light across the items placed in the top chamber 14.

Accompanying any embodiment of interior material, the exterior of the cabinet 10 may be comprised of plastic, plastic including microbe-resistant materials, or metals. The preferred metal for appearance and durability is stainless steel, but copper and aluminum are also viable alternatives.

Alternatively, the exterior of the cabinet 10 may be comprised of composite materials including wood, carbon fiber, or types of glass and plastic.

If the inner lining 18 of the top chamber 14 is comprised of metal, it may be connected to a voltage source in order to generate repulsion of electrostatically charged atomized liquid chemical injected into the top chamber 14, improving effectiveness at driving chemical treatments toward the garments placed therein. The inner lining 18 of the top chamber 14 should then be electrically insulated from unintended sources of grounding, for example by mounting the inner lining 18 to the cabinet 10 using plastic brackets or using insulating washers and inserts anywhere that the inner lining 18 will be fastened to metal brackets.

In the preferred embodiment, the inner lining 18 will be so thin as to have a low heat capacity, allowing it to rapidly heat during the steam cycle and rapidly cool before the user opens the top chamber 14 and makes skin contact.

Between the inner lining 18 and outer walls of the cabinet 10 there is a thermally and electrically insulating outer lining 20. Insulating materials within the outer lining 20 may include fiberglass, fabrics, cellulosic materials, structures to create multiple air gaps, or expanding foams.

Paths for necessary wiring and plumbing, for example to support additional chemical delivery nozzles or wiring for ultraviolet lighting 44 and the control mechanism 34, may be inserted within the outer lining 20. The preferred method of manufacture would be to insert in the interstitial zone 22, also known as the empty space between the outer lining 20 and the wall of the top chamber 14, wiring and plumbing channels, such as the thin-walled metal pipes commonly used for electric conduit, the flexible metal pipes commonly used for electrical conduit, or plastic pipes commonly used for electric conduit, with all bends being so gradual as to permit "fishing tape" to be threaded through them, which is commonly used in electrical installations to facilitate drawing wires and tubing through narrow channels. Once the conduits have been installed in the interstitial zone 22, the remaining empty space between the outer lining 20 and the wall of the top chamber 14 may be filled with an expanding foam which will create a highly-insulating layer.

Alternatively, the inner lining 18 may first be wrapped in the outer lining 20 of insulating foam or fabric, then the conduits as described above may be affixed, then the inner lining 18, the outer lining 20, and the conduits may be wrapped in another layer of insulating foam or fabric.

Alternatively, conduits and channels for wiring may penetrate perpendicularly through both the inner lining 14 and the walls of the cabinet 10 and travel visibly along the outer surface of the cabinet 10 before re-entering bottom chamber 16 or another location on the cabinet 10.

Alternatively, conduits and channels for wiring may be fabricated into the structure of the internal wall of the cabinet 10, traveling along the internal surface of the cabinet 10 wall until arriving at a point or multiple points adjacent to the bottom chamber 16, and from that point or those points penetrating in a perpendicular direction from the internal surface of the cabinet 10, through the outer lining 20, and to the inner lining 14.

In the preferred embodiment, the delivery nozzle 24 will penetrate directly from the bottom chamber 16 into the internal surface of the top chamber 14, with all points of penetration sealed to prevent escape of steam, chemicals, or process gases into the bottom chamber 16. The preferred location for the delivery nozzle 24 will be in the base of one corner of the top chamber 14, furthest removed from the user-accessible cabinet door 12, with the delivery nozzle 24 oriented to direct atomized liquid chemical vertically. However, in alternative embodiments, other delivery nozzle 24 locations throughout the internal surface of the top chamber 14 may be used for chemical delivery, and those locations may be connected to the bottom chamber 16 by the appropriate process connections via any of the conduit and channel schemes described above.

The apparatus may contain baffles in the top chamber 14 that slightly restrict but do not altogether prevent the egress of steam, air, and other substances introduced by the bottom chamber 16. Alternatively, the apparatus may include a vent to permit gases and other substances to escape to a safe remote location.

Alternatively, the apparatus may have mechanical, manual, or fixed louvers or be entirely sealed to accommodate an internal pressure and increase the saturation temperature of steam to accelerate the antibacterial effects of steam within the top chamber 14. If so sealed, the apparatus will include a primary and potentially a secondary pressure relief valve for safety.

The cabinet 10 includes a cabinet door 12 with a latching mechanism and an interlock device that prevents the active components of the cabinet 10 from operating while the cabinet door 12 is open. Any face of the cabinet 10 may serve as the cabinet door 12, whether the front, back, side, top, or bottom. The cabinet door 12 may include a hinge mechanism that permits it to swing free of the path of any garments or objects placed into the top chamber 14. The cabinet door 12 may include a gasket that allows it to seal.

In one embodiment, ultraviolet light is generated by multiple sodium discharge lamps.

In another embodiment, ultraviolet light is generated by mercury discharge lamps.

In another embodiment, ultraviolet light is generated by multiple ultraviolet fluorescent tubes.

In the preferred embodiment, ultraviolet light is generated by multiple ultraviolet LEDs installed in many locations throughout the interior of the top chamber 14.

In all embodiments using ultraviolet lights 44, the ultraviolet lights 44 are installed in a wide enough disbursement to ensure that light falls on all outside surfaces of lab coats or other items introduced into the top chamber 14.

Ultraviolet lights 44 may be installed into recessed outlets. They may be protected from steam by materials that do not stop the ultraviolet light, including but not limited to ultraviolet-transparent formulations of glass and plastic. The ultraviolet lights 44 may be accessible from the inside of the top chamber 14 for replacement. Any protective materials may be removable to enable easy access to the ultraviolet lights 44. Alternatively, the apparatus may be designed to allow access to the ultraviolet lights 44 from the exterior of the cabinet 10.

Ultraviolet lights 44 may also be installed on movable structures internal to the top chamber 14 that enable them to be inserted inside objects such as lab coats or shoes, in order to ensure that internal surfaces receive a dose of ultraviolet light as well as external surfaces. These movable structures may be available as separate, removable additions to the top chamber 14 and may be connected to the interior of the top chamber 14 via easily-disconnected electrical connectors. The connectors may include caps that protect them against chemicals, steam, and corrosion when not in use.

The ultraviolet lights 44 may include an interlock mechanism that stops electricity if the door is open, ensuring safety for operators.

To increase efficacy of the ultraviolet lights 44, their housings and the interior of the top chamber 14 may have mirrors or reflective metals installed to ensure light traveling in non-useful directions is reflected onto the objects introduced into the top chamber 14. Mirrors may be "first-surface" mirrors in which the exposed surface is treated with silvering materials instead of the posterior surface; this will increase the efficacy of the mirrors to reflect ultraviolet light, which may be attenuated while passing twice through many forms of glass and plastic in ordinary mirrors.

Chemical treatment may be delivered through one or more delivery nozzles 24. Gas pressure for the nozzles may be generated in one of four ways: Via an air compressor 26 controlled electrically and flowing directly to the delivery nozzle 24, via an air compressor 26 connected through an air accumulating vessel and controlled both electrically and with a valve restricting air flow from the accumulating vessel, via a steam generator 30 controlled electrically and with valves and a pump to restrict water supply, or via a steam generator 30 controlled electrically and with valves and a pump to restrict water supply and additionally controlled through an accumulating vessel and a valve to restrict steam flow from the accumulating vessel. Delivery nozzles 24 may atomize chemicals by way of high-speed gas flow, electrostatic vaporization, low-speed mixed streams, heat, or other methods. In addition, delivery nozzles 24 may include electrical elements to ionize the atomized chemicals, resulting in a more even adherence to the surface of items introduced into the top chamber 14. In the preferred embodiment, the delivery nozzle 24 should be an electrostatic induction spray-charging nozzle device, the device being adapted for use with an electrical power supply, a liquid source and a gas source upstream of a rearward end of the device, comprising: an electrically insulated body portion having a first channel therethrough for carrying a liquid from the liquid source, and a second channel therethrough for carrying gas from the gas source; a liquid orifice tip in the body portion, the liquid orifice tip having an aperture aligned to receive and discharge liquid from the first channel of the body portion, the liquid being discharged from the liquid tip so as to meet with the gas in a droplet formation zone and form an atomized spray cloud; a removable cap coupled to a forward end of the body portion, the cap comprising a spray exit aperture substantially coaxial to the liquid orifice tip aperture, an electrode forming a portion of the aperture, and an electrical connector within the cap for connecting the electrode to the power supply; the body portion containing (1) no seam through which fluid may communicate with the first channel and (2) no electrical path between the first channel and the exterior of the body portion through which electrical charge may leak from the electrode to the liquid in the first channel; and at least one resilient seal located between the body portion and the cap and not in communication with the first channel in order to block any fluid communication between the liquid orifice tip of the body and the electrical connector in the cap.

Chemical treatment may instead be delivered by spraying a mist of chemical into the atmosphere of the enclosure using pumps to power a pressurized delivery mechanism similar to fuel injectors in automobiles, alone or in combination with fans, blowers, or stirrers to agitate the air and ensure chemical is dispersed across the surface of items introduced into the top chamber 14.

Chemical treatment may instead or in addition be delivered by vaporizing chemicals through electrostatically-controlled delivery channels in a manner similar to inkjet printer heads or thermally-controlled bubble-jet printer heads.

Chemical treatment may instead be delivered by feeding chemicals into the space by gravity from small openings at the top, alone or in combination with agitating the air with fans or other mechanical means to ensure uniform adherence to the items introduced into the space.

Chemicals may delivered from one or multiple reservoirs 28. Reservoirs 28 may be refillable from externally-accessible inlets, but reservoirs 28 may alternatively or in addition be designed to be removable and replaceable with identical reservoirs. Replacement reservoirs may include electronic devices to make their contents readily known to the controller for the apparatus. Such devices may include radio frequency identification (RFID) chips, data chips accessible by direct contact with electrodes, bar codes, conductive labels, or electrodes connected to manually-adjustable switches. Replacement reservoirs and the slots in the apparatus meant to accept them may also include voids, slots, or brackets designed to accept such electronic devices in the future.

In addition to such electromechanical controls as pressure switches, temperature switches, and pressure control valves, the apparatus may include electronic control circuits with computing and communications capability. Such circuits and communications devices may come preinstalled into the apparatus, but the apparatus may also include slots, brackets, sockets, and voids intended to accommodate upgraded or additional electronics.

The basic functions of the apparatus may be enhanced by an electronic control mechanism 34.

The electronic control mechanism 34 may have inputs from sensors. Sensors may include photocells adjacent to the ultraviolet lights 44 inside the top chamber 14, which can assess whether the ultraviolet lights 44 are delivering the expected level of ultraviolet light. Sensors may also include electric meters for the ultraviolet lights 44. Sensors may also include pressure meters for compressed air or steam accumulators, for water pump discharge lines, or for steam or compressed air discharge pressures entering the delivery nozzle 24. Sensors may also include temperature meters for compressed air or steam accumulators, for the inside of the top chamber 14, or for heating elements installed in steam generators 30. Sensors may also include liquid level meters for removable chemical reservoirs 28, water reservoirs 28, or steam generation pressure vessels. Sensors may also include commercially-available devices designed to cause biological material to luminesce, in combination with camera assemblies or light meters that can evaluate the effectiveness of the disinfection procedure. Sensors may also include scanners capable of reading Radio Frequency Identification (RFID) chips, Near Field Communication (NFC) devices, and electrical direct contact patches for data chips.

The electronic control mechanism 34 will be able to automatically operate any mechanisms of the apparatus that are not operated via direct feedback loops from sensors, including setting the temperature and pressure of steam, switching heating elements on and off and modulating their intensity, switching ultraviolet lights on and off and modulating their intensity, actuating internal safety interlocks, adjusting louvers if installed, setting the positions of valves, and setting the set points of control valves. Automatic operation of these mechanisms may be accomplished through wireless interfaces or through directly wired connections, using outputs such as an open or closed circuit, an on-or-off voltage, a range of voltages to specify a range or response, pulse-width modulation, digital optical signals, or digital connections such as serial and USB. All of these outputs are common modes of control for programmable logic controllers (PLCs) and commercially-available prototyping kits.

The control mechanism 34 will include an operating system capable of executing a basic program and receiving updates to it. The program will be aware of the invention's unique serial number identification and the treatment regimens available to the user, including multiple chemical reservoirs and durations of treatment. It may also be aware of the price charged for each treatment. The treatment regimens available will be displayed on the control mechanism 34. The control mechanism 34 will at a minimum be able to display the type of treatment regimen selected—this can be effected preferably with a basic LCD or LED display such as those commonly found in calculators. This can be effected even more simply by the use of small lights behind translucent symbols and text, similar to the techniques commonly used in automobile dashboards. The control mechanism 34 may also be capable of displaying artwork in multiple colors—this can be effected using many commercially-available small LCD, LED, or OLED display units or successive generations of technology that display information on a small modular display. The control mechanism 34 will allow the user to operate the selection mechanism in a simple way, for example turning a large knob in the center of multiple displays that represent multiple treatment regimen.

The control mechanism 34 may use a user identification module which may either be integral to its hardware or may be removable and replaceable with multiple commercially-available user identification modules. The need for a replaceable user identification module is to adapt to authentication techniques widely in use in hospitals and other end users' industries. A common form of user identification is the non-contact security badge, which links to a unique employee and is always worn to gain access to different parts of the building. These badges may require reading by near-field communication, RFID proximity scanners, or other forms of direct electrical contact as are commonly used on smart card devices, magnetic stripe, and many other means. Some means of reading the card are interactive and may require an external data connection and a loadable security routine in the control mechanism 34. Other identification modules which may be needed could include RFID readers or barcode readers that scan the garment introduced into the space, biometric readers that use an external data connection to request authentication of a user's unique attributes, and integrated electronic payment systems. The control mechanism 34 will include several common and adaptable modes of interconnection and the apparatus will include adaptable voids, brackets, and slots designed to accommodate a variety of common identification modules. In addition, the control mechanism 34 will have the ability to store a code library, either remotely installable or locally installable via a connection such as a USB port that is able to provide necessary software support for such interchangeable identification modules. Therefore, the control mechanism 34 for the apparatus can be connected to a variety of plug-and-play modules in order to identify or receive payment from users in a variety of customer settings.

In the preferred embodiment, the control mechanism 34 will use an Internet connection module to transfer data to a remote data center. The Internet connection module may connect to Internet infrastructure already existing within the building in which it is installed via common wired or wireless connections such as Ethernet, Wi-Fi, Bluetooth, industrial wireless, or may connect to outside Internet not provided in the building via common wired or wireless connections such as cable Internet, DSL, dial-up modem, or cellular data. The Internet connection may be integrated into the control mechanism 34 but may in addition or alternatively be connected via a separate replaceable module, allowing the Internet connection to be easily upgraded or replaced by future data protocols not yet known.

In one embodiment of a control cycle, the control mechanism 34 will allow the user to identify via whatever means is commonly used in the customer setting, such as an RFID tag embedded in the user's lab coat which is read immediately upon entering the lab coat into the top chamber 14. Upon reading the identification, the control mechanism 34 will use its Internet connection to verify authorization to bill a disinfection cycle by encrypting the identification information for safety and then transmitting it via its Internet connection to a remote data center. In that data center, the identification information will be verified through whatever payment method the customer has put in place, for example verifying that the lab coat has been registered in the hospital's payment system and, if not, whether the hospital will pay a general fee for an unverified garment. If authentication is approved, the data center will transmit an encrypted authorization code to the control mechanism 34 by means of its Internet connection. The control mechanism 34 will then indicate via its user interface that the user is authorized to run a disinfection cycle—for example, the cycle selection knob may have a large button in the center of it which turns from a red LED light to a green LED light. The user will then use the cycle selection knob to select the disinfection cycle options desired and press the button. The control mechanism 34 will then transmit a voltage to the safety interlock mechanism in the cabinet door 12, which will lock the cabinet door 12 closed for safety. The control mechanism 34 will load the parameters including set points and limits for the cycle chosen. The control mechanism 34 will then begin to charge the steam generator 30, for example by transmitting a voltage to a pump to introduce water into the steam generator 30 pressure vessel until a level switch is activated, indicating that the water is high enough. Simultaneously, the control mechanism 34 will transmit a voltage to the heating element in the steam generator 30, causing it to produce heat so long as the temperature sensor in the heating element does not exceed safe limits. If the temperature or pressure in the steam generator 30 is below the lower limit of the target temperature or pressure, the control mechanism 34 will continue to transmit voltage to the heating element. If the temperature of pressure in the steam generator 30 rises above the upper limit of the target temperature or pressure, the control mechanism 34 will deactivate or decrease the voltage to the heating element. During this time, first the control mechanism 34 will activate the ultraviolet lights 44 in the top chamber 14 for the intensity and time required by the cycle chosen. Then the control mechanism 34 will deactivate the ultraviolet lights 44 and begin to transmit steam at a targeted rate, achieving the target by monitoring the pressure upstream of the delivery nozzle 24 and adjusting the steam release valve via a continuous control loop, while steam pressure continues to build in the steam generator 30 pressure vessel. As soon as both the required minimum steam cycle time has passed and sufficient pressure has built in the steam generator 30 pressure vessel, the control mechanism 34 will perform several tasks. It will activate a selector valve which connects the treatment chemical from the correct chemical reservoir 28 for the cycle chosen to the delivery nozzle 24. It will increase the steam delivery rate by setting the correct pressure for chemical delivery to the control mechanism 34 upstream of the delivery nozzle 24 and opening the steam release valve until that pressure is achieved. It will adjust the steam release valve via a continuous control loop. It will measure the amount of delivery via one of a few methods: it may measure the volume of steam delivery by either monitoring the change in pressure in the steam generator 30 pressure vessel or by measuring the duration of steam release with a timer while monitoring the pressure upstream of the delivery nozzle 24, or it may measure the amount of treatment chemical delivered via a fluid flow meter or via change in the level of the treatment chemical reservoir 28. It may use a combination of these measurement techniques to correlate measurements and increase accuracy, or to diagnose indications of trouble in the delivery nozzle's 24 performance. Once the correct amount of chemical has been delivered, the control mechanism 34 will close the chemical selection valve and the steam delivery valve. The control mechanism 34 will then wait for the period of time determined by the cycle chosen. It will then send a voltage to a dry heater and air fan, which will evacuate the steam and chemicals from the top chamber 14 and ensure the lab coat or other item inserted into the top chamber 14 is dried and ready for use. Once the cycle is complete, the control mechanism 34 will then send a signal to a speaker to produce an audible indication, change the output and/or color of the user interface display, and deactivate the safety interlock, allowing the user to extract the lab coat or other item inserted into the top chamber 14. The control mechanism 34 will use its Internet connection to transmit a report on the cycle completed and any instrument measurements required by its operating program to a remote data center, allowing that data center to correlate billing and meter data to a time, cabinet, cycle chosen, and user identification or billing information. During the off time, or during times of peak use, the control mechanism may be directed either as its normal mode or by command via its Internet connection to maintain the peak temperature and pressure of the steam generator 30, ensuring the apparatus remains immediately available for another cycle.

The invention may be embodied in other forms without departing from the spirit and the essential attributes as described here. The particular embodiments described here explain several methods whereby a professional of reasonable skill might be able to replicate the invention but do not reduce the scope of the claims. Reference should be made to the appended Claims, rather than to the details of the Description here, in order to determine the scope of the invention.

What is claimed is:

1. An apparatus for disinfecting lab coats, shoes, other textiles, and other objects, comprising:
   a) a cabinet comprising:
      i) a top chamber having a flat bottom, opposing side walls, a top wall, a rear wall, and a front having an opening with a latch-able door assembly for closing the opening; and
      ii) a bottom chamber having a flat bottom, opposing side walls, a top wall, a rear wall, a front opening to allow insertion and removal of a service drawer, said bottom chamber having access holes located on one of the side walls or the rear wall for nesting multiple cabinets together or for allowing electrical or plumbing connections, said top chamber being oriented directly above said bottom chamber;
   b) an inner lining, which may or may not be electrostatically charged, located inside said top chamber which contains a rod located on the inner surface of the top wall running axially from the front to rear of said top chamber;
   c) an outer lining of electrical and thermal insulation surrounding said inner lining;
   d) an interstitial zone located outside of said outer lining and inside said first chamber with channels for wiring, plumbing, and sensors, as well as slots, brackets, and voids to accommodate possible upgrades;

e) an electrostatically charged delivery nozzle located inside said top chamber, positioned in such a way as to evenly disperse chemical and antimicrobial treatments across the surface of garments or objects inserted into said top chamber;

f) a compressor located in said bottom chamber and connected to said delivery nozzle capable of generating either high velocity air or high velocity steam in order to atomize chemical or antimicrobial fluids;

g) a control mechanism located on the outside of said cabinet;

h) a service drawer located in said bottom chamber which contains various reservoirs and generators for storing and pumping the fluids which are sent to said delivery nozzle, said service drawer being capable of sliding in and out of said bottom chamber; and i) a supporting member or hanger being capable of gliding on and off of said rod in said top chamber.

2. An apparatus as recited in claim 1 further comprising ultraviolet-C lights installed along the inner walls of said top chamber in such a way as to ensure even disbursement of light onto the outer surface of garments or objects inserted into said top chamber.

3. An apparatus as recited in claim 1 further comprising a means for detecting and authenticating the garments or equipment placed inside said top chamber, such as a radio-frequency identification (RFID) scanner.

4. An apparatus as recited in claim 1 further comprising ultraviolet-C lights installed along the inner walls of said top chamber in such a way as to ensure even disbursement of light onto the outer surface of garments or objects inserted into said top chamber and a means for detecting and authenticating the garments or equipment placed inside said top chamber, such as a radio-frequency identification (RFID) scanner.

5. An apparatus as recited in either claim 1, 2, 3, or 4 in which the control mechanism is a manual control mechanism located on the outside of said cabinet capable of operating the various functions of the apparatus.

6. An apparatus as recited in either claim 1, 2, 3, or 4 in which the control mechanism is a programmable electronic controller located on the outside of said cabinet capable of operating the various functions of the apparatus.

7. An apparatus as recited in claim 5 further comprising means for said controller to communicate with other computers over information networks, such as the Internet.

\* \* \* \* \*